US005478849A

United States Patent [19]

Hanasaki et al.

[11] Patent Number: 5,478,849

[45] Date of Patent: Dec. 26, 1995

[54] THIADIAZOLE DERIVATIVE, PROCESS FOR PRODUCING IT AND AGRICULTURAL AND HORTICULTURAL FUNGICIDE USING IT AS AN ACTIVE INGREDIENT

[75] Inventors: Yasuaki Hanasaki; Hiroyuki Watanabe, both of Kanagawa; Kimio Katsuura, Tokyo; Masatoshi Fujiwara, Fukushima; Teruhiko Ide, Yamaguchi, all of Japan

[73] Assignee: Tosoh Corporation, Tokyo, Japan

[21] Appl. No.: 230,789

[22] Filed: Apr. 21, 1994

[30] Foreign Application Priority Data

Apr. 21, 1993 [JP] Japan .................................... 5-094253
Apr. 21, 1993 [JP] Japan .................................... 5-094254

[51] Int. Cl.[6] ......................... C07D 285/10; A01N 43/82

[52] U.S. Cl. ............................................ 514/362; 548/135

[58] Field of Search .............................. 548/135; 514/362

[56] References Cited

U.S. PATENT DOCUMENTS 4,555,521 11/1985 Engel et al. ............................ 514/362

FOREIGN PATENT DOCUMENTS 0414511 2/1991 European Pat. Off. .
2181527 12/1973 France .

OTHER PUBLICATIONS

Potts, Comprehensive Heterocyclic Chemistry vol. 6 p. 537 (1984).

*Primary Examiner*—Robert Gerstl
*Attorney, Agent, or Firm*—Sughrue, Minn, Zinn, Macpeak & Seas

[57] ABSTRACT

Disclosed is (a) 1,2,5-thiadiazole derivatives represented by the following formulae [I] or [III]:

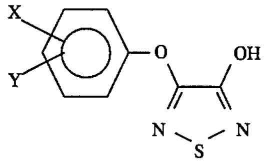

[I]

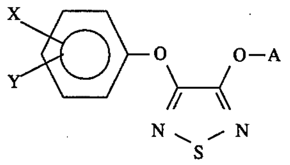

[III]

wherein X and Y are the same or different and each represents a hydrogen atom, a halogen atom, an alkyl group having from 1 to 6 carbon atoms, an alkoxy group having from 1 to 4 carbon atoms, a nitro group, a trifluoromethyl group, a carboxyl group, an alkoxycarbonyl group having from 2 to 5 carbon atoms, a naphthyl group or a tetrahydronaphthyl group; and A represents an alkyl group having from 1 to 6 carbon atoms, —C(=O)$OR^1$, —C(=O)$NR^2R^3$, a phenyl group which may be substituted by at least one of an alkyl group having from 1 to 6 carbon atoms and an alkoxy group having from 1 to 4 carbon atoms, —$CHR^4$C(=O)$R^5$ or —C(=O)$R^6$, in which $R^1$ represents an alkyl group having from 1 to 6 carbon atoms, $R^2$ and $R^3$ are the same or different and each represents a hydrogen atom or an alkyl group having from 1 to 6 carbon atoms, $R^4$ represents a hydrogen atom or an alkyl group having from 1 to 4 carbon atoms, $R^5$ represents an alkoxy group having from 1 to 4 carbon atoms or an amino group which may be substituted by at least one of an alkyl group having from 1 to 4 carbon atoms and a phenyl group which may be substituted by at least one halogen atom, and $R^6$ represents an alkyl group having from 1 to 6 carbon atoms, (b) a process for producing the compound represented by formula [I] and (c) an agricultural and horticultural fungicide comprising the compound represented by formula [III].

3 Claims, No Drawings

THIADIAZOLE DERIVATIVE, PROCESS FOR PRODUCING IT AND AGRICULTURAL AND HORTICULTURAL FUNGICIDE USING IT AS AN ACTIVE INGREDIENT

FIELD OF THE INVENTION

The present invention relates to a novel 1,2,5-thiadiazole derivative and a production process thereof. The 1,2,5-thiadiazole derivative of the present invention is a compound useful as an intermediate for organic compounds and an intermediate for medicines and agricultural chemicals.

Furthermore, the present invention relates to another novel 1,2,5-thiadiazole derivative and also to an agricultural and horticultural fungicide containing it as an active ingredient.

BACKGROUND OF THE INVENTION

3-Alkoxy-4-hydroxy-1,2,5-thiadiazoles are described in *Journal of Organic Chemistry*, page 2823 (1967). However, the thiadiazole derivative of the present invention represented by formula [I] described below and the production process thereof have not been known. Further, the thiadiazole derivative of the present invention represented by formula [III] described below and the agricultural and horticultural fungicide containing the thiadiazole derivative as an active ingredient have not been known.

Further, many compounds having a fungicidal activity are utilized in agriculture but various problems such as the tolerance for plant pathogenic fungi is revealed by continuously using the same or similar chemicals for a long period of time have been indicated and hence the development of novel agricultural and horticultural fungicides which do not reveal such tolerance has been desired.

SUMMARY OF THE INVENTION

Accordingly, an object of the present invention is to provide a novel thiadiazole derivative useful as an intermediate for organic compounds and an intermediate for medicines and agricultural chemicals and also to provide a production process thereof.

Another object of the present invention is to provide a novel agricultural and horticultural fungicide.

These and other objects of the present invention have been achieved by a 1,2,5-thiadiazole derivative represented by the following formula [I]:

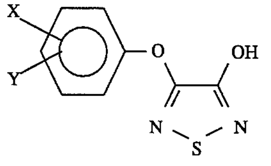

[I]

wherein X and Y are the same or different and each represents a hydrogen atom, a halogen atom, an alkyl group having from 1 to 6 carbon atoms, an alkoxy group having from 1 to 4 carbon atoms, a nitro group, a trifluoromethyl group, a carboxyl group, an alkoxycarbonyl group having from 2 to 5 carbon atoms, a naphthyl group or a tetrahydronaphthyl group.

Further, these and other objects of the present invention have been achieved by a process for producing the 1,2,5-thiadiazole derivative represented by formula [I] described above, which comprises the step of reacting a 1,2,5-thiadiazole derivative represented by the following formula [II] with a base:

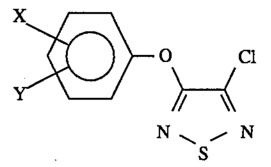

[II]

wherein X and Y are the same as described above, respectively.

Furthermore, these and other objects of the present invention have been achieved by a 1,2,5-thiadiazole derivative represented by the following formula [III]:

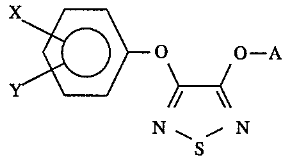

[III]

wherein X and Y are the same as described above, respectively, and A represents an alkyl group having from 1 to 6 carbon atoms, —C(=O)OR$^1$ (wherein R$^1$ represents an alkyl group having from 1 to 6 carbon atoms), —C(=O)NR$^2$R$^3$ (wherein R$^2$ and R$^3$ are the same or different and each represents a hydrogen atom or an alkyl group having from 1 to 6 carbon atoms), a phenyl group which may be substituted by at least one of an alkyl group having from 1 to 6 carbon atoms and an alkoxy group having from 1 to 4 carbon atoms, —CHR$^4$C(=O)R$^5$ (wherein R$^4$ represents a hydrogen atom or an alkyl group having from 1 to 4 carbon atoms and R$^5$ represents an alkoxy group having from 1 to 4 carbon atoms or an amino group which may be substituted by at least one of an alkyl group having from 1 to 4 carbon atoms and a phenyl group which may be substituted by at least one halogen atom) or —C(=O)R$^6$ (wherein R$^6$ represents an alkyl group having from 1 to 6 carbon atoms).

Moreover, these and other objects of the present invention have been achieved by an agricultural and horticultural fungicide comprising the 1,2,5-thiadiazole derivative represented by formula [III] as an active ingredient.

DETAILED DESCRIPTION OF THE INVENTION

The present invention will now be described in more detail.

In the compounds represented by formulae [I], [II], and [III] described above, examples of the alkyl groups having from 1 to 6 carbon atoms include straight chain, branched or cyclic alkyl groups having from 1 to 6 carbon atoms such as a methyl group, an ethyl group, an n-propyl group, an isopropyl group, an n-butyl group, an isobutyl group, an s-butyl group, a t-butyl group, an n-pentyl group, a cyclopentyl group, an n-hexyl group and a cyclohexyl group.

Examples of the alkyl groups having from 1 to 4 carbon atoms include straight chain, branched or cyclic alkyl groups having from 1 to 4 carbon atoms such as a methyl group, an ethyl group, an n-propyl group, an isopropyl group, an n-butyl group, an isobutyl group, an s-butyl group and a t-butyl group.

Examples of the alkoxy groups having from 1 to 4 carbon atoms include a methoxy group, an ethoxy group, an isopropoxy group, an n-butoxy group, an isobutoxy group, an s-butoxy group and a t-butoxy group.

Examples of the alkoxycarbonyl groups having from 2 to 5 carbon atoms include a methoxycarbonyl group, an ethoxycarbonyl group, an isopropoxycarbonyl group, an n-butoxycarbonyl group, an isobutoxycarbonyl group, an s-butoxycarbonyl group and a t-butoxycarbonyl group.

Examples of the halogen atoms include a fluorine atom, a chlorine atom, a bromine atom and an iodine atom.

The 1,2,5-thiadiazole derivative represented by formula [II], which is used as a starting material for producing the 1,2,5-thiadiazole derivative of the present invention represented by formula [I], can be obtained by the process described, e.g., in JP-A-3-193771 (the term "JP-A" as used herein means an "unexamined published Japanese patent application").

According to the production process of this invention, the 1,2,5-thiadiazole derivative represented by formula [II] is reacted with a base in water in the presence or absence of an organic solvent at a temperature of from −10° C. to 120° C., preferably from 30° C. to 80° C., for from few minutes to 24 hours, preferably from 1 hour to 6 hours.

Examples of the organic solvent used in the above reaction include aromatic hydrocarbons (for example, benzene, toluene, xylene), ethers (for example, diethyl ether, tetrahydrofuran, dioxane), halogenated hydrocarbons (for example, dichloromethane, carbon tetrachloride), amines (for example, pyridine, triethylamine), alcohols (for example, methanol, ethanol, isopropanol), and polar solvents (for example, N,N-dimethylformamide, dimethyl sulfoxide, 1,3 -dimethyl-2-imidazolidinone, hexamethyltriamide phosphate).

Example of the base used in the foregoing reaction, include organic bases (for example, pyridine, triethylamine), inorganic bases (for example, sodium hydroxide, potassium hydroxide, sodium carbonate), and alkali metal alkoxides (for example, sodium methoxide, sodium ethoxide).

In the reaction, the base is used in an amount of from 1 to 10 equivalents, preferably from 1 to 3 equivalents, per one equivalent of the 1,2,5-thiadiazole derivative represented by formula [II].

Thus, the 1,2,5-thiadiazole derivative represented by formula [I] is obtained.

The compound of the present invention represented by formula [III] described above can be produced by the following production process. Example of Production Process 1:

The 3-aryloxy-4-hydroxy-1,2,5-thiadiazole represented by formula [I] described above is reacted with a compound represented by the formula A—Q (wherein A has the same meaning as described above and Q represents a halogen atom) in an organic solvent in the presence of a base at a temperature of from 0° C. to 150° C., preferably from 20° C. to 100° C., for from few minutes to 24 hours, preferably from 1 hour to 6 hours. The compound represented by the formula A—Q is used in an amount of from 1 to 3 equivalents and the base is used in an amount of from 1 to 5 equivalents, each per one equivalent of the 3 -aryloxy-4-hydroxy-1,2,5-thiadiazole represented by formula [I]. Example of Production Process 2:

The 3-aryloxy-4-chloro-1,2,5-thiadiazole represented by formula [II] described above is reacted with a phenol derivative in an organic solvent in the presence of a base at a temperature of from 20° C. to 150° C., preferably from 80° C. to 130° C., for from few minutes to 24 hours, preferably from 3 hours to 12 hours. The phenol derivative is used in an amount of from 1 to 3 equivalents and the base is used in an amount of from 1 to 5 equivalents each per one equivalent of the 3 -aryloxy-4-chloro-1,2,5-thiadiazole represented by formula [II].

Examples of the organic solvent used in the foregoing reactions include aromatic hydrocarbons (for example, benzene, toluene, xylene), ethers (for example, diethyl ether, tetrahydrofuran, dioxane), halogenated hydrocarbons (for example, dichloromethane, carbon tetrachloride), amines (for example, pyridine, triethylamine), alcohols (for example, methanol, ethanol, isopropanol) and polar solvents (for example, N,N-dimethylformamide, dimethyl sulfoxide, 1,3 -dimethyl-2-imidazolidinone, hexamethyltriamide phosphate).

Examples of the base used in the above reactions include organic bases (for example, pyridine, triethylamine) inorganic bases (for example, sodium hydroxide, potassium hydroxide, sodium carbonate) and alkali metal alkoxides (for example, sodium methoxide, sodium ethoxide).

The 1,2,5-thiadiazole derivative of the present invention represented by formula [III] described above can be utilized as an agricultural and horticultural fungicide. That is, the compound represented by formula [III] has an excellent fungicidal activity to plant pathogenic fungi and can be applied for the extermination and eradication of plant diseases by various fungi in a wide range.

Examples of the plant diseases to which the compound represented by formula [III] can be applied include rice blast (Pyricularia oryzae), rice sheath blight (*Rhizoctonia solani*), apple powdery mildew (*Podosphaera leucotricha*), apple scab (*Venturia inaequalis*), pear scab (*Venturia nashicola*), pear blossom blight (*Sclerotinia mali*), Japanese persimmon anthracnose (*Gloeosporium kaki*), peach brown rot (*Sclerotinia cinerea*), peach scab (*Cladosporium carpophilum*), grape gray mold (*Botrytis cinerea*), grape anthracnose (*Elsinoe ampelina*), grape ripe rot (*Glomerella cingulata*), sugar beet cercospora leaf spot (*Cercospora beticola*), peanut leaf spot (*Cercospora arachidicola*), peanut leaf spot (*Cercospora personata*), barley powdery mildew (*Erysiphe graminis* f. sp. *hordei*), wheat eye spot (*Pseudocercosporella herpotrichoides*), barley snow mold (*Fusarium nivale*), wheat powdery mildew (*Erysiphe graminis* f. sp. *tritici*), wheat leaf rust (*Puccinia recondita*), cucumber downy mildew (*Pseudoperonospora cubansis*), cucumber powdery mildew (*Sphaerotheca fuliginea*), cucumber gummy stem blight (*Mycosphaerella melonis*) , cucumber gray mold (*Botrytis cinerea*), cucumber scab (*Cladosporium cucumerinum*), tomato late blight (*Phytophthora infestans*), tomato leaf mold (*Cladosporium fulvum*), tomato gray mold (*Botrytis cinerea*), strawberry powdery mildew (*Sphaerotheca humuli*) , common hop gray mold (*Botrytis cinerea*), tobacco powdery mildew (*Erysiphe cichoracearum*), rose black spot (*Diplocarpon rosae*), citrus fruit scab (*Elsinoe fawcetii*), citrus fruit blue mold (*Penicillium italicum*) and citrus fruit common green mold (*Penicillium digitaturn*). In these diseases, the compound represented by formula [III] shows a remarkable effect to rice blast (*Pyricularia oryzae*) and wheat leaf rust (*Puccinia recondita*).

Also, since the compound represented by formula [III] has the feature that it has no phytotoxicity to cultivated plants in an ordinary use concentration, the compound can be conveniently used as an agricultural and horticultural fungicide to the plant diseases due to plant pathogenic fungi.

For the agricultural and horticultural fungicide according to the present invention, the thiadiazole derivative represented by formula [III] may be used by itself but usually is used as a preparation such as a wettable powder, an emulsion, a dusting powder or granules being compounded with a carrier, a surface active agent, a dispersing agent or an adjuvant, according to a usual way.

Further, the thiadiazole derivative of the present invention can be used as a pharmaceutically acceptable salt thereof.

Such a preparation is applied after being diluted to a proper concentration or is directly applied.

The compounding ratio of the active ingredient is selected according to the necessary purpose but is usually from 0.5 to 80% by weight to the amount of the preparation.

The applying amount of the agricultural and horticultural fungicide of the present invention depends upon the kind of the compound used as the active ingredient, the extent of the disease and the damage, the environmental conditions and the kind of the preparation used, but when the fungicide is used in situ as a dusting powder or granules, the applying amount is generally from 0.1 kg to 5 kg, and preferably from 0.3 kg to 1 kg, per 10 ares as the active ingredient. Also, in the case of final use in a liquid form such as an emulsion or a wettable powder, the concentration of the fungicide is generally from 0.1 ppm to 10,000 ppm, preferably from 10 ppm to 3,000 ppm.

The compound of the present invention represented by formula [I] described above is a compound useful as an intermediate for organic compounds and an intermediate for medicines and agricultural chemicals.

Also, the compound of the present invention represented by formula [III] described above has an excellent fungicidal activity, in particular, has an excellent fungicidal activity to plant pathogenic fungi, and can be applied for the extermination and eradication of plant diseases by various fungi in a wide range.

Further, the compounds of the present invention can be widely used as medicines.

The present invention is now illustrated in greater detail by reference to the following examples which, however, are not to be construed as limiting the invention in any way.

In addition, all parts in these examples, unless otherwise indicated, are by weight.

Example 1

Production of 3-hydroxy-4-(4-methoxyphenoxy)-1,2,5-thiadiazole:

To a solution formed by dissolving 4.37 g of 3-chloro-4-(4-methoxyphenoxy)-1,2,5-thiadiazole in 40 ml of dimethyl sulfoxide was added 40 ml of an aqueous solution of 2.5M potassium hydroxide and the mixture was stirred for 3 hours at 80° C. After allowing to cool to room temperature and washing twice the reaction mixture with ether, the aqueous layer was acidified with hydrochloric acid and extracted with ether. The ether layer was washed three times with diluted hydrochloric acid and then once with an aqueous saturated sodium chloride solution, and after drying the solution with anhydrous magnesium sulfate, the solvent was distilled off.

By recrystallizing the residue from a mixture of hexane and chloroform, 2.66 g of 3-hydroxy-4-(4-methoxyphenoxy)-1,2,5-thiadiazole was obtained.

Melting Point: 141° to 142° C. $^1$H-NMR (solvent: $CDCl_3$, unit: δ ppm): 3.83(s,3H), 6.9 to 7.0(m,2H), 7.2 to 7.3(m,2H) IR (KBr, $cm^{-1}$): 3200 to 2500, 1565, 1530, 1505, 1320, 1230, 1190, 875 Elemental Analysis (%) for $C_9H_8N_2O_3S$: Found: C 48.25, H 3.39, N 12.73 Calculated: C 48.20, H 3.59, N 12.49.

Other examples of the present invention represented by formula [I] obtained by similar processes as described above are shown in Table 1 below and the properties of each compounds are shown in Table 2 below.

TABLE 1

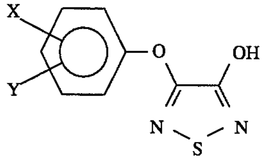

| Compound No. | X | Y |
|---|---|---|
| 1 | H | 2-$COOCH_3$ |
| 2 | H | 4-$C(CH_3)_3$ |
| 3 | H | 4-$CF_3$ |
| 4 | H | 4-F |
| 5 | H | 4-$NO_2$ |
| 6 | H | 4-Cl |
| 7 | 2-Cl | 4-Cl |
| 8 | 2-Cl | 6-Cl |
| 9 | H | H |
| 10 | H | 3-Cl |
| 11 | H | 2-Cl |
| 12 | H | 4-$CH_3$ |
| 13 | 3-COOH | 4-$NO_2$ |
| 14 | 3-Cl | 4-Cl |

TABLE 2

| Compound No. | Properties: | $^1$H-NMR (solvent: $CDCl_3$, unit: δ ppm)<br>IR (KBr, $cm^{-1}$)<br>Melting point (°C.)<br>Elemental analysis (%) |
|---|---|---|
| 1 | Melting point: | 115 to 116° C. |
| | $^1$H-NMR: | 3.84(s, 3H), 7.3 to 7.5(m, 2H), 8.0 to 8.1(m, 1H), 9.2(bs, 1H) |
| | IR: | 3300 to 2800, 1700, 1540, 1440, 1310, 1295, 1270, 1215, 1200 |
| | Elemental analysis for $C_{10}H_8N_2O_4S$ | |
| | Found: | C 47.34, H 3.34, N 11.34 |
| | Calculated: (Cald.) | C 47.61, H 3.19, N 11.10 |
| 2 | Melting point: | 159 to 161° C. |
| | $^1$H-NMR: | 1.36(s, 9H), 7.28(d, J=9Hz, 2H), |

TABLE 2-continued

| Compound No. | Properties: | $^1$H-NMR (solvent: $CDCl_3$, unit: δ ppm)<br>IR (KBr, $cm^{-1}$)<br>Melting point (°C.)<br>Elemental analysis (%) |
|---|---|---|
| | | 7.46(d, J=9Hz, 2H) |
| | IR: | 3200 to 2500, 1560, 1520, 1510, 1230, 1195, 1130 |
| | Elemental analysis for $C_{12}H_{14}N_2O_2S$ | |
| | Found: | C 57.90, H 5.46, N 10.86 |
| | Cald: | C 57.58, H 5.63, N 11.19 |
| 3 | Melting point: | 145 to 148° C. |
| | $^1$H-NMR: | 7.49(d, J=8.4Hz, 2H), 7.72(d, J=8.4Hz, 2H) |
| | IR: | 3200 to 2500, 2560, 1560, 1510, 1330, 1230, 1175, 1130, 1070 |
| | Elemental analysis for $C_9H_5N_2O_2SF_3$ | |
| | Found: | C 40.99, H 1.86, N 10.48 |
| | Cald.: | C 41.22, H 1.92, N 10.68 |
| 4 | Melting point: | 175 to 176° C. |
| | $^1$H-NMR: | 7.1 to 7.5(m) (acetone-d6) |
| | IR: | 3200 to 2400, 1570, 1500, 1235, 1215, 1180, 880 |
| | Elemental analysis for $C_8H_5N_2O_2SF$ | |
| | Found: | C 45.50, H 2.44, N 13.29 |
| | Cald.: | C 45.28, H 2.37, N 13.20 |
| 5 | Melting point: | 201 to 202° C. |
| | $^1$H-NMR: | 7.64(d, J-9.2Hz, 1H), 8.37(d, J=9.2Hz, 1H) (acetone-d6) |
| | IR: | 3200 to 2500, 1560, 1520, 1515, 1490, 1350, 1300, 1240 |
| | Elemental analysis for $C_8H_5N_3O_4S$ | |
| | Found: | C 39.83, H 2.07, N 17.93 |
| | Cald.: | C 40.17, H 2.10, N 17.56 |
| 6 | Melting point: | 185 to 186° C. |
| | $^1$H-NMR: | 7.24(d, J=9.3Hz, 1H), 7.30(d, J=9.3Hz, 1H) (acetone-d6) |
| | IR: | 3100 to 2500, 1560, 1520, 1490, 1240, 1195, 1090, 1020, 880 |
| | Elemental analysis for $C_8H_5N_2O_2SCl$ | |
| | Found: | C 41.85, H 2.36, N 12.02 |
| | Cald.: | C 42.02, H 2.20, N 12.25 |
| 7 | Melting point: | 156 to 157° C. |
| | $^1$H-NMR: | 7.5 to 7.7(m) (acetone-d6) |
| | IR: | 3100 to 2500, 1560, 1520, 1475, 1320, 1250, 1230, 1100 |
| | Elemental analysis for $C_8H_4N_2O_2SCl_2$ | |
| | Found: | C 36.19, H 1.48, N 10.39 |
| | Cald.: | C 36.52, H 1.53, N 10.64 |
| 8 | Melting point: | 155 to 157° C. |
| | $^1$H-NMR: | 7.41(dd, J=7.2, 8.8Hz, 1H), 7.5 to 7.7(m, 2H)(acetone-d6) |
| | IR: | 3200 to 2500, 1560, 1450, 1240, 1205 |
| | Elemental analysis for $C_8H_4N_2O_2SCl_2$ | |
| | Found: | C 36.73, H 1.63, N 10.36 |
| | Cald.: | C 36.52, H 1.53, N 10.64 |
| 9 | Melting point: | 130 to 132° C. |
| | $^1$H-NMR: | 7.2 to 7.6(m) (acetone-d6) |
| | IR: | 3200 to 2400, 1560, 1525, 1520, 1490, 1230, 880, 760 |
| | Elemental analysis for $C_8H_6N_2O_2S$ | |
| | Found: | C 49.74, H 2.94, N 14.03 |
| | Cald.: | C 49.47, H 3.11, N 14.42 |
| 10 | Melting point: | 118 to 120° C. |
| | $^1$H-NMR: | 6.8 to 7.6(m) |
| | IR: | 3200 to 2500, 1560, 1550, 1520, 1510, 1475, 1320, 1235, 885 |
| | Elemental analysis for $C_8H_5N_2O_2SCl$ | |
| | Found: | C 41.72, H 2.32, N 12.11 |
| | Cald.: | C 42.02, H 2.20, N 12.25 |

TABLE 2-continued

| Compound No. | Properties: | $^1$H-NMR (solvent: $CDCl_3$, unit: δ ppm)<br>IR (KBr, $cm^{-1}$)<br>Melting point (°C.)<br>Elemental analysis (%) |
|---|---|---|
| 11 | Melting point: | 146 to 148° C. |
| | $^1$H-NMR: | 7.2 to 7.6(m) (acetone-d6) |
| | IR: | 3200 to 2500, 1560, 1525, 1475, 1265, 1235, 875, 760 |
| | Elemental analysis for $C_8H_5N_2O_2SCl$ | |
| | Found: | C 41.86, H 2.09, N 11.88 |
| | Cald.: | C 42.02, H 2.20, N 12.25 |
| 12 | Melting point: | 167 to 168° C. |
| | $^1$H-NMR: | 2.34(s, 3H), 7.15 to 7.35(m, 4H) (acetone-d6) |
| | IR: | 3200 to 2500, 1560, 1530, 1510, 1320, 1235, 1190, 880 |
| | Elemental analysis for $C_9H_8N_2O_2S$ | |
| | Found: | C 51.85, H 3.69, N 13.40 |
| | Cald.: | C 51.91, H 3.87, N 13.45 |
| 13 | Melting point: | 210° C. (decomp.) |
| | $^1$H-NMR: | 7.78(dd, J=2.6, 9.0Hz, 1H), 7.88(d, J=2.6Hz, 1H), 8.15(d, J=9Hz, 1H) (acetone-d6) |
| | IR: | 3300 to 2400, 1720, 1650, 1540, 1360, 1290 |
| | Elemental analysis for $C_9H_5N_3O_6S$ | |
| | Found: | C 38.52, H 1.90, N 14.62 |
| | Cald.: | C 38.16, H 1.77, N 14.83 |
| 14 | Melting point: | 181 to 183° C. |
| | $^1$H-NMR: | 7.40(dd, J=2.8, 8.8Hz, 1H), 7.68(d, J=8.8Hz, 1H), 7.70(d, J=2.8Hz, 1H) (acetone-d6) |
| | IR: | 3200 to 2500, 1560, 1525, 1470, 1235, 1190, 1125, 1030 |
| | Elemental analysis for $C_8H_4N_2O_2SCl_2$ | |
| | Found: | C 36.33, H 1.34, N 10.94 |
| | Cald.: | C 36.52, H 1.53, N 10.64 |

Example 2

Production of 3-phenoxy-1,2,5-thiadiazol-4-yl N,N-dimethylcarbamate (Compound No. 31):

In acetonitrile were suspended 0.80 g of 3-hydroxy-4 -phenoxy-1,2,5-thiadiazole and 0.46 g of potassium carbonate and after adding 0.36 g of dimethylcarbamoyl chloride to the suspension, the mixture was refluxed for 12 hours. After allowing to cool, the reaction mixture was poured in water and extracted with ether. The ether layer was washed twice each time with a diluted aqueous solution of sodium hydroxide, water, and then a saturated aqueous sodium chloride solution. The ether layer thus washed was dried with anhydrous magnesium sulfate, concentrated, and thereafter purified by silica gel column chromatography to provide 0.85 g of 3-phenoxy-1,2,5 -thiadiazol-4-yl N,N-dimethylcarbamate.

Melting point: Oily product $^1$H-NMR (solvent: $CDCl_3$, unit: δ ppm): 2.90(s,3H), 3.00(s,3H), 7.0 to 7.3(m,5H) IR (neat, $cm^{-1}$): 1750, 1490, 1475, 1470, 1220, 1150 Elemental analysis (%) for $C_{11}H_{11}N_3O_3S$ Found: C 49.55, H 4.25, N 16.08 Calculated: C 49.80, H 4.17, N 15.83

Example 3

Production of 3,4-bis(4-t-butylphenoxy)-1,2,5-thiadiazole (Compound No. 32):

To a suspension formed by suspending 0.16 g of sodium hydride (60%) in N,N-dimethylformamide was added 0.6 g of 4-t-butylphenol and after stirring the mixture for one hour at 60° C., 0.81 g of 3-(4-t-butylphenoxy)-4-chloro-1,2,5-thiadiazole was added to the mixture followed by stirring for 12 hours at 100° C. After allowing to cool, the reaction mixture was poured in water and extracted with ether. The ether layer collected was washed twice each time with a diluted aqueous sodium hydroxide solution, water, and then a saturated aqueous sodium chloride solution. The ether layer thus washed was dried with anhydrous magnesium sulfate, concentrated, and purified by silica column chromatography to provide 0.84 g of 3,4-bis(4-t-butylphenoxy)-1, 2,5 -thiadiazole.

Melting point: 104° to 108° C. $^1$H-NMR (solvent: $CDCl_3$, unit: δ ppm): 1.38(s,9H), 7,31(d,J=8.7 Hz,2H), 7,48(d,J=8.7 Hz,2H) IR (KBr, $cm^{-1}$): 2960, 1530, 1510, 1475, 1255, 1235 Elemental analysis (%) for $C_{22}H_{26}N_2O_2S$ Found: C 68.91, H 6.89, N 7.65 Calculated: C 69.07, H 6.85, N 7.32

Also, examples of the compounds of the present invention represented by formula [III] obtained by the similar processes as above are shown in Table 3 below and the properties of each compound are shown in Table 4 below.

TABLE 3

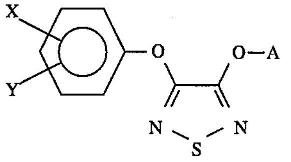

| Compound No. | X | Y | A |
|---|---|---|---|
| 15 | H | 4-Cl | $-CH_3$ |
| 16 | H | $4-NO_2$ | $-C(=O)N(CH_3)_2$ |
| 17 | H | 4-Cl | $-C(=O)N(CH_3)_2$ |
| 18 | 2-Cl | 4-Cl | $-C(=O)N(CH_3)_2$ |
| 19 | 2-Cl | 4-Cl | $-CH(CH_3)COOCH_3$ |
| 20 | H | 2-Cl | $-C(=O)N(CH_3)_2$ |
| 21 | H | 3-Cl | $-C(=O)N(CH_3)_2$ |
| 22 | 2-Cl | 6-Cl | $-C(=O)CH(CH_3)_2$ |
| 23 | 2-Cl | 6-Cl | $-C(=O)N(CH_3)_2$ |
| 24 | H | $2-COOCH_3$ | $-CH_3$ |
| 25 | H | $4-OCH_3$ | 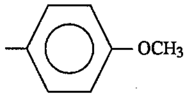 |
| 26 | H | $4-CH_3$ | 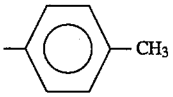 |
| 27 | H | 4-Cl | $-COOCH_3$ |
| 28 | 3-Cl | 4-Cl | $-COOCH_3$ |
| 29 | H | 2-COOH | $-CH_3$ |
| 30 | H | H | $-CH_2C(=O)N(CH_3)-$ 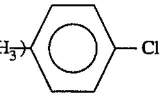 |

TABLE 4

| Compound No. | Properties: $^1$H-NMR (solvent: $CDCl_3$, unit: δ ppm) IR (KBr, $cm^{-1}$) Melting point (°C.) Elemental analysis (%) |
|---|---|
| 15 | Melting point: 82 to 83° C.<br>$^1$H-NMR: 4.10(s,3H), 7.0 to 7.4(m,4H)<br>IR: 1550, 1495, 1490, 1420, 1265, 1240, 1010<br>Elemental analysis for $C_9H_7N_2O_2SCl$<br>Found: C 44.46, H 2.98, N 11.44<br>Calculated: C 44.54, H 2.90, N 11.54 (Cald.) |
| 16 | Melting point: 99 to 103° C.<br>$^1$H-NMR: 4.0(s,3H), 4.10(s,3H), 7.1 to 7.4(m,2H), 8.0 to 8.3(m,2H)<br>IR: 1725, 1520, 1345, 1230, 1170<br>Elemental analysis for $C_{11}H_{10}N_4O_5S$<br>Found: C 42.54, H 3.14, N 17.84<br>Cald.: C 42.58, H 3.24, N 18.05 |
| 17 | Melting point: oily product<br>$^1$H-NMR: 2.95(s,3H), 3.10(s,3H), 7.0 to 7.4(m,4H)<br>IR: 1750, 1490, 1470, 1385, 1225, 1215, 1150 (neat)<br>Elemental analysis for $C_{11}H_{10}N_3O_3SCl$<br>Found: C 44.40, H 3.43, N 14.38<br>Cald.: C 44.08, H 3.36, N 14.01 |
| 18 | Melting point: 53 to 54° C.<br>$^1$H-NMR: 1.68(d,J=7Hz,3H), 3,78(s,3H), 5.30(q,J=7Hz,lH), 7.2 to 7.5(m,3H)<br>IR: 1750, 1535, 1495, 1490, 1475, 1225, 1105<br>Elemental analysis for $C_{12}H_{10}N_2O_4SCl_2$<br>Found: C 41.18, H 2.86, N 8.04<br>Cald.: C 41.27, H 2.88, N 8.02 |
| 19 | Melting point: oily product<br>$^1$H-NMR: 3.00(s,3H), 3.10(s,3H), 7.1 to 7.5(m,3H)<br>IR: 1740, 1480, 1390, 1230, 1160 (neat)<br>Elemental analysis for $C_{11}H_9N_3O_3SCl_2$<br>Found: C 39.85, H 2.78, N 12.87<br>Cald.: C 39.53, H 2.71, N 12.57 |
| 20 | Melting point: oily product<br>$^1$H-NMR: 3.00(s,3H), 3.10(s,3H), 7.1 to 7.6(m,4H)<br>IR: 1750, 1475, 1385, 1225, 1150 (neat)<br>Elemental analysis for $C_{11}H_{10}N_3O_3SCl$<br>Found: C 43.98, H 3.33, N 13.76<br>Cald.: C 44.08, H 3.36, N 14.01 |
| 21 | Melting point: oily product<br>$^1$H-NMR: 2.97(s,3H), 3.07(s,3H), 7.0 to 7.4(m,4H)<br>IR: 1750, 1470, 1385, 1220, 1150 (neat)<br>Elemental analysis for $C_{11}H_{10}N_3O_3SCl$<br>Found: C 43.79, H 3.42, N 13.63<br>Cald.: C 44.08. H 3.36, N 14.01 |
| 22 | Melting point: 136 to 141° C.<br>$^1$H-NMR: 1.40(d,J=7Hz,6H), 2.90(septet., J=7Hz,1H), 7.0 to 7.5(m,3H)<br>IR: 1780, 1460, 1450, 1240, 1070<br>Elemental analysis for $C_{12}H_{10}N_2O_3SCl_2$<br>Found: C 43.14, H 3.08, N 8.66<br>Cald.: C 43.25, H 3.02, N 8.40 |
| 23 | Melting point: 102 to 105° C.<br>$^1$H-NMR: 3.03(s,3H), 3.13(s,3H), 7.0 to 7.5(m,3H)<br>IR: 1750, 1745, 1470, 1450, 1380, 1240, 1195, 1145<br>Elemental analysis for $C_{11}H_9N_3O_3SCl_2$<br>Found: C 39.61, H 2.76, N 12.49<br>Cald.: C 39.53, H 2.71, N 12.57 |
| 24 | Melting point: 93 to 95° C.<br>$^1$H-NMR: 3.77(s,3H), 4.20(s,3H), 7.2 to 7.4(m,2H), 7.5 to 7.7(m,1H), 8.0 to 8.1(m,1H)<br>IR: 1720, 1550, 1510, 1490, 1425, 1270, 1235, 1090<br>Elemental analysis for $C_{11}H_{10}N_2O_4S$<br>Found: C 49.82, H 3.79, N 10.47<br>Cald.: C 49.61, H 3.78, N 10.52 |
| 25 | Melting point: 105 to 106° C.<br>$^1$H-NMR: 3.77(s,3H), 6.83(d,J=9Hz,2H), 7.17(d,J=9Hz,2H)<br>IR: 1500, 1480, 1220, 1180, 1035<br>Elemental analysis for $C_{16}H_{14}N_2O_4S$ |

TABLE 4-continued

| Compound No. | Properties: $^1$H-NMR (solvent: $CDCl_3$, unit: δ ppm) IR (KBr, $cm^{-1}$) Melting point (°C.) Elemental analysis (%) |
|---|---|
| | Found: C 58.31, H 4.15, N 8.81<br>Cald.: C 58.17, H 4.27, N 8.47 |
| 26 | Melting point: 65 to 66° C.<br>$^1$H-NMR: 2.38(s,3H), 7.25(s,4H)<br>IR: 1505, 1475, 1250, 1230, 1205, 1195<br>Elemental analysis for $C_{16}H_{14}N_2O_{2S}$<br>Found: C 64.08, H 4.85, N 9.50<br>Cald.: C 64.41, H 4.72, N 9.38 |
| 27 | Melting point: oily product<br>$^1$H-NMR: 3.99(s,3H), 7.25(d,J=10Hz,2H), 7.39(d,J=10Hz,2H)<br>IR: 1785, 1490, 1470, 1270, 1220, 1210 (neat)<br>Elemental analysis for $C_{10}H_7N_2O_4SCl$<br>Found: C 42.25, H 2.64, N 10.04<br>Cald.: C 41.89, H 2.46, N 9.77 |
| 28 | Melting point: 48 to 50° C.<br>$^1$H-NMR: 3.99(s,3H), 7.20(dd,J=2.9,8.8Hz,1H), 7.47(d,J=2.9Hz,1H), 7.50(d,J=8.8Hz,1H)<br>IR: 1795, 1470, 1250, 1230, 1220, 1200<br>Elemental analysis for $C_{10}H_6N_2O_4SCl_2$<br>Found: C 37.45, H 1.69, N 8.73<br>Cald.: C 37.40, H 1.88, N 8.72 |
| 29 | Melting point: 163 to 165° C.<br>$^1$H-NMR: 4.19(s,3H), 7.3 to 7.5(m,2H), 7.68(dt,J=1.8,7.8Hz,1H), 8.14(dd,J=1.8,7.8Hz,1H)<br>IR: 3300 to 2800, 1720, 1510, 1420, 1270, 1245, 1215<br>Elemental analysis for $C_{10}H_8N_2O_4S$<br>Found: C 47.30, H 3.13, N 11.20<br>Cald.: C 47.61, H 3.19, N 11.10 |
| 30 | Melting point: 127 to 129° C.<br>$^1$H-NMR: 3.30(s,3H), 4.81(s,2H), 7.1 to 7.5(m,9H)<br>IR: 1685, 1545, 1500, 1490, 1420, 1230<br>Elemental analysis for $C_{17}H_{14}N_3O_3SCl$<br>Found: C 54.07, H 3.80, N 11.18<br>Cald.: C 54.33, H 3.75, N 11.18 |

Example 4

Preparation of Wettable Powder:

A mixture of 10 parts of the compound (Compound No. 16) of the present invention, 87.3 parts of Zieclite (trade name, made by Kunimine Industrial Co., Ltd.) as a carrier material, 1.35 parts of Neopelex (trade name, made By Kao Atlas Co., Ltd.) and 1.35 parts of Sorpol 800A (trade name, made by Toho Chemical Industrial Co., Ltd.) as surface active agents was ground to provide a wettable powder containing 10% of the compound of the present invention.

Example 5

Preparation of Emulsion:

By emulsifying 5 parts of the compound (Compound No. 17) of the present invention in 85 parts of xylene together with 10 parts of Sorpol 800A as a surface active agent, an emulsion containing 5% of the compound of the present invention was obtained.

Example 6

Preparation of Dusting Powder:

A uniform mixture of 2 parts of the compound (Compound No. 18) of the present invention, 5 parts of diatomaceous earth, and 93 parts of clay was ground to provide a dusting powder containing 2% of the compound of the present invention.

Example 7

Preparation of Granules:

A mixture of 10 parts of the compound (Compound No. 19) of the present invention, 50 parts of bentonite, 35 parts of Kunilite (trade name, made by Kunimine Industrial Co., Ltd.), and 5 parts of Sorpol 800A as a surface active agent was ground, 10 parts of water was added to the ground mixture followed by uniformly mixing, the mixture was extruded through sieve openings of 0.7 mm in diameter, and after drying, the extruded product was cut into lengths of from 1 to 2 mm to provide granules containing 10% of the compound of the present invention.

Example 8

Rice blast preventing effect test:

Rice plant seeds (plant breeding: yamahoushi) were sowed in a plastic pot of 8 cm×8 cm and grown under glass. At 2.5- to 3-foliate stage, a solution obtained by diluting a wettable powder prepared according to the same manner as in Example 4 with water such that the concentration of the active ingredient became 500 ppm was applied thereover. After air-drying, rice blast fungi (*Pyricularia oryzae*) were inoculated and the pot was placed in a chamber kept at a temperature of 25° C. At 7 days after the inoculation, the number of disease spots of the whole pot was determined and the preventive value was calculated by the following formula.

$$\text{Preventive value (\%)}=(1-A/B)\times 100$$

A: Number of disease spots in the treated section

B: Number of disease spots in the non-treated section

The results are shown in Table 5 below.

TABLE 5

| Compound No. | Concentration (ppm) | Preventive value (%) |
|---|---|---|
| 17 | 500 | 93 |
| 19 | 500 | 97 |
| 20 | 500 | 100 |
| 21 | 500 | 99 |
| 27 | 500 | 100 |
| 28 | 500 | 90 |
| 32 | 500 | 95 |

As is apparent from the results shown in Table 5, the compounds represented by formula [III] have an excellent fungicidal activity.

Example 9

Wheat leaf rust prevention effect test:

Wheat seeds (plant breeding: Norin No. 61) were sowed in a plastic pot of 8 cm×8 cm and grown under glass. Then, a solution obtained by diluting the wettable powder prepared as in Example 4 with water such that the concentration became a definite concentration was applied onto the wheat young seedling having the completely developed first leaf. After air-drying, wheat leaf rust fungi (*Puccinia recondita*) were inoculated and the pot was placed in a chamber kept at 25° C. At 7 days after the inoculation, the number of the disease spots of the whole pot were determined and the preventive value was calculated by the formula as shown in Example 8.

The results are shown in Table 6 below.

TABLE 6

| Compound No. | Concentration (ppm) | Preventive value (%) |
|---|---|---|
| 17 | 50 | 99 |
| 27 | 250 | 80 |
| 28 | 250 | 86 |

As is apparent from the results shown in Table 6, the compounds represented by formula [III] have an excellent fungicidal activity.

While the present invention has been described in detail and with reference to specific embodiments thereof, it is apparent to one skilled in the art that various changes and modifications can be made therein without departing from the spirit and the scope of the present invention.

What is claimed is:

1. A 1,2,5-thiadiazole derivative represented by the following formula [I]:

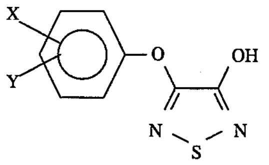

[I]

wherein X and Y are the same or different and each represents a hydrogen atom, a halogen atom, an alkyl group having from 1 to 6 carbon atoms, an alkoxy group having from 1 to 4 carbon atoms, a nitro group, a trifluoromethyl group, a carboxyl group, an alkoxycarbonyl group having from 2 to 5 carbon atoms, a naphthyl group or a tetrahydronaphthyl group.

2. A 1,2,5-thiadiazole derivative represented by the following formula [III]:

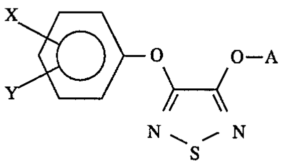

[III]

wherein X and Y are the same or different and each represents a hydrogen atom, a halogen atom, an alkyl group having from 1 to 6 carbon atoms, an alkoxy group having from 1 to 4 carbon atoms, a nitro group, a trifluoromethyl group, a carboxyl group, an alkoxycarbonyl group having from 2 to 5 carbon atoms, a naphthyl group or a tetrahydronaphthyl group; and A represents an alkyl group having from 1 to 6 carbon atoms, $-C(=O)OR^1$, $-C(=O)NR^2R^3$, a phenyl group which may be substituted by at least one of an alkyl group having from 1 to 6 carbon atoms and an alkoxy group having from 1 to 4 carbon atoms, $-CHR^4C(=O)R^5$ or $-C(=O)R^6$, in which $R^1$ represents an alkyl group having from 1 to 6 carbon atoms;

$R^2$ and $R^3$ are the same or different and each represents a hydrogen atom or an alkyl group having from 1 to 6 carbon atoms;

$R^4$ represents a hydrogen atom or an alkyl group having from 1 to 4 carbon atoms;

$R^5$ represents an alkoxy group having from 1 to 4 carbon atoms or an amino group which may be substituted by at least one of an alkyl group having from 1 to 4 carbon atoms and a phenyl group which may be substituted by at least one halogen atom; and $R^6$ represents an alkyl group having from 1 to 6 carbon atoms.

3. An agricultural and horticultural fungicide comprising a 1,2,5-thiadiazole derivative represented by the following formula [III] as an active ingredient:

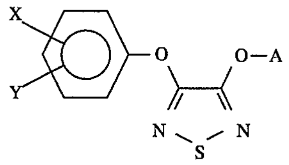

[III]

wherein X and Y are the same or different and each represents a hydrogen atom, a halogen atom, an alkyl group having from 1 to 6 carbon atoms, an alkoxy group having from 1 to 4 carbon atoms, a nitro group, a trifluoromethyl group, a carboxyl group, an alkoxycarbonyl group having from 2 to 5 carbon atoms, a naphthyl group or a tetrahydronaphthyl group; and A represents an alkyl group having from 1 to 6 carbon atoms, $-C(=O)OR^1$, $-C(=O)NR^2R^3$, a phenyl group which may be substituted by at least one of an alkyl group having from 1 to 6 carbon atoms and an alkoxy group having from 1 to 4 carbon atoms, $-CHR^4C(=O)R^5$ or $-C(=O)R^6$, in which $R^1$ represents an alkyl group having from 1 to 6 carbon atoms;

$R^2$ and $R^3$ are the same or different and each represents a hydrogen atom or an alkyl group having from 1 to 6 carbon atoms;

$R^4$ represents a hydrogen atom or an alkyl group having from 1 to 4 carbon atoms;

$R^5$ represents an alkoxy group having from 1 to 4 carbon atoms or an amino group which may be substituted by at least one of an alkyl group having from 1 to 4 carbon atoms and a phenyl group which may be substituted by at least one halogen atom; and $R^6$ represents an alkyl group having from 1 to 6 carbon atoms.

* * * * *